(12) United States Patent
Niwa et al.

(10) Patent No.: US 9,816,904 B2
(45) Date of Patent: Nov. 14, 2017

(54) ANALYZING METHOD OF SPOT WELDED PORTION, ANALYZING PROGRAM OF SPOT WELDED PORTION, RECORDING MEDIUM AND ANALYZING APPARATUS OF SPOT WELDED PORTION

(71) Applicant: NIPPON STEEL & SUMITOMO METAL CORPORATION, Tokyo (JP)

(72) Inventors: Toshiyuki Niwa, Tokyo (JP); Shunji Hiwatashi, Tokyo (JP); Akihiro Uenishi, Tokyo (JP); Satoshi Hirose, Tokyo (JP); Yusuke Kamada, Tokyo (JP); Akira Shirai, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 218 days.

(21) Appl. No.: 14/652,698

(22) PCT Filed: Dec. 17, 2012

(86) PCT No.: PCT/JP2012/082700
§ 371 (c)(1),
(2) Date: Jun. 16, 2015

(87) PCT Pub. No.: WO2014/097378
PCT Pub. Date: Jun. 26, 2014

(65) Prior Publication Data
US 2015/0330881 A1 Nov. 19, 2015

(51) Int. Cl.
*G01N 3/02* (2006.01)
*B23K 31/12* (2006.01)
(Continued)

(52) U.S. Cl.
CPC .............. *G01N 3/02* (2013.01); *B23K 31/12* (2013.01); *G01M 17/0078* (2013.01); *G06F 17/5018* (2013.01); *G06F 17/5095* (2013.01)

(58) Field of Classification Search
CPC .............. B23K 31/12; G01M 17/0078; G06F 17/5018; G06F 17/5095; G01N 3/02
See application file for complete search history.

(56) References Cited

U.S. PATENT DOCUMENTS

| 2001/0044706 A1 | 11/2001 | Yoshikawa et al. | |
| 2007/0090165 A1* | 4/2007 | Kumagai | B23K 11/34 228/101 |

(Continued)

FOREIGN PATENT DOCUMENTS

| CN | 1771434 A | 5/2006 |
| CN | 101739490 A | 6/2010 |

(Continued)

OTHER PUBLICATIONS

Extended European Search Report dated Apr. 4, 2016, for European Application No. 12890376.2.

(Continued)

*Primary Examiner* — Francis Gray
(74) *Attorney, Agent, or Firm* — Birch, Stewart, Kolasch & Birch, LLP

(57) ABSTRACT

An analyzing method of a spot welded portion, includes: acquiring bar elements as the spot welded portion; extracting other bar elements existing at a periphery of a target bar element which is targeted among the acquired bar elements; determining whether or not there is a bar element which shares the same end point with the target bar element among the extracted bar elements; determining that the target bar element and the bar element which shares the same end point with the target bar element are a three-layer spot welded portion when it is determined that there is the bar element which shares the same end point with the target bar element; and determining whether or not there is a bar element whose distance between elements with the target bar element is within a predetermined distance among the extracted bar (Continued)

elements when it is determined that there is not the bar element which shares the same end point with the target bar element, and determining that the target bar element and the extracted bar element are not the three-layer spot welded portion when it is determined that there is not the bar element within the predetermined distance.

8 Claims, 17 Drawing Sheets

(51) Int. Cl.
  *G06F 17/50* (2006.01)
  *G01M 17/007* (2006.01)

(56) References Cited

U.S. PATENT DOCUMENTS

| | | | |
|---|---|---|---|
| 2009/0211366 A1* | 8/2009 | Tomioka | G01N 3/00 73/841 |
| 2010/0131256 A1 | 5/2010 | Hallquist | |
| 2013/0000415 A1 | 1/2013 | Yoshida et al. | |
| 2015/0161295 A1* | 6/2015 | Arita | G06F 17/50 703/1 |

FOREIGN PATENT DOCUMENTS

| | | |
|---|---|---|
| EP | 2191928 A1 | 6/2010 |
| JP | 10-172008 A | 6/1998 |
| JP | 11-102383 A | 4/1999 |
| JP | 2005-148053 A | 6/2005 |
| JP | 2005-315854 A | 11/2005 |
| JP | 2007-90366 A | 4/2007 |
| JP | 2007-93286 A | 4/2007 |
| JP | 2007-114046 A | 5/2007 |
| JP | 2007-304005 A | 11/2007 |
| JP | 2008-108242 A | 5/2008 |
| JP | 2009-237672 A | 10/2009 |
| JP | 2010-127933 A | 6/2010 |
| JP | 2011-221644 A | 11/2011 |
| WO | WO 2004/099761 A1 | 11/2004 |
| WO | WO 2011/126057 A1 | 10/2011 |

OTHER PUBLICATIONS

Palmonella et al., "Finite element models of spot welds in structural dynamics: review and updating," Computers and Structures, vol. 83, 2005 (Available online Jan. 11, 2005), pp. 648-661.
Translation of the International Preliminary Report on Patentability (Chapter I, Form PCT/IB/338, Form PCT/IB/373), Issued in PCT/JP2012/082700, dated Jul. 2, 2015.
Translation of the Written Opinion of the International Searching Authority (PCT/ISA/237), issued in PCT/JP2012/082700, dated Mar. 12, 2013.
International Search Report, issued in PCT/JP2012/082700, dated Mar. 12, 2013.
Office Action issued in Taiwanese Patent Application No. 101147784, dated Sep. 23, 2014.
Written Opinion of the International Searching Authority, issued in PCT/JP2012/082700, dated Mar. 12, 2013.

* cited by examiner

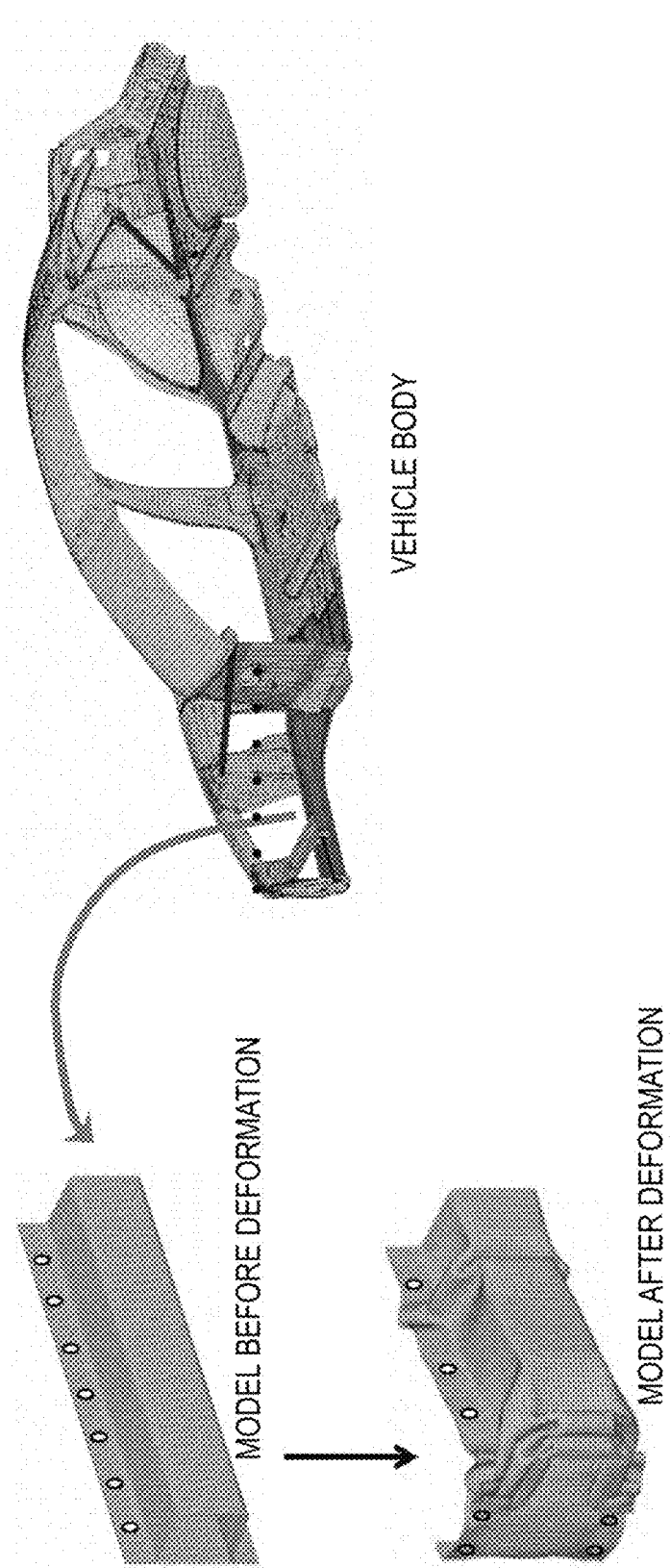

FIG.5

COMPONENT NUMBER 1

BASE MATERIAL INFORMATION

| BASE MATERIAL NUMBER | CROSS SECTIONAL INFORMATION NUMBER |
|---|---|
| 1 | 1 |

CROSS SECTIONAL INFORMATION

| CROSS SECTIONAL INFORMATION NUMBER | elform | shrt | nip | propt | gr/irid | icomp | setyp |
|---|---|---|---|---|---|---|---|
| 1 | 2 | 0.833333 | 3 | 0 | 0 | 0 | 0 |
| SHEET THICKNESS t1 | SHEET THICKNESS t2 | SHEET THICKNESS t3 | SHEET THICKNESS t4 | nloc | marea | idof | edgset |
| 1.400000 | 1.400000 | 1.400000 | 1.400000 | 0.000 | 0.000 | 0.000 | 0 |

FIG.6

| SHELL ELEMENT INFORMATION | | | | | |
|---|---|---|---|---|---|
| ELEMENT NUMBER | COMPONENT NUMBER TO WHICH ELEMENT BELONGS | NODE POINT NUMBER CONSTITUTING ELEMENT | | | |
| | | n1 | n2 | n3 | n4 |
| 1 | 1 | 23 | 10 | 11 | 12 |
| 2 | 1 | 7 | 8 | 9 | 24 |
| 3 | 1 | 24 | 9 | 10 | 23 |
| 4 | 1 | 21 | 25 | 13 | 14 |
| 5 | 1 | 25 | 23 | 12 | 13 |
| 6 | 2 | 35 | 36 | 46 | 42 |
| 7 | 2 | 42 | 46 | 45 | 41 |
| 8 | 2 | 36 | 37 | 44 | 46 |
| 9 | 2 | 46 | 44 | 43 | 45 |
| 10 | 2 | 47 | 49 | 35 | 36 |

FIG.7

| NODE POINT INFORMATION | | | |
|---|---|---|---|
| NODE POINT NUMBER | COORDINATE | | |
| | x | y | z |
| 1 | -12.6999998 | 40.0000000 | 0 |
| 2 | -12.6999998 | 37.5000076 | 0 |
| 3 | -12.6999998 | 30.5000057 | 0 |
| 4 | -12.6999998 | 23.5000019 | 0 |
| 5 | -12.6999998 | 16.4999981 | 0 |
| 6 | -12.6999998 | 9.5000019 | 0 |
| 7 | -12.6999998 | 2.5000095 | 0 |

| END POINT INFORMATION | | | |
|---|---|---|---|
| END POINT NUMBER | COORDINATE | | |
| | x | y | z |
| 1 | -12.6999998 | 0.000 | 0 |
| 2 | -9.3665333 | 0.000 | 0 |
| 3 | -6.0330667 | 0.000 | 0 |

| ELEMENT NUMBER | END POINT NUMBER CONSTITUTING ELEMENT | | REPRESENTATIVE POINT NUMBER |
|---|---|---|---|
| | n1 | n2 | |
| 1 | 50 | 52 | 200 |
| 2 | 54 | 56 | 201 |
| ... | ... | ... | ... |
| 155 | 193 | 194 | 300 |
| 156 | 194 | 195 | 301 |
| 157 | 196 | 197 | 302 |

BAR ELEMENT INFORMATION

ANALYZING METHOD OF SPOT WELDED PORTION, ANALYZING PROGRAM OF SPOT WELDED PORTION, RECORDING MEDIUM AND ANALYZING APPARATUS OF SPOT WELDED PORTION

TECHNICAL FIELD

The present invention relates to an analyzing method of a spot welded portion, an analyzing program of the spot welded portion, a recording medium and an analyzing apparatus of the spot welded portion. For example, it is suitable to be used when an analyzing object having a lot of spot welded portions such as a vehicle body of an automobile is fracture analyzed.

BACKGROUND ART

For example, in automotive industry, it has been studied to make a structural member absorb an impact energy to enable a vehicle body structure capable of reducing injury for passengers at a collision time. There is a front side member in major structural members which is made absorb the impact energy at a full-lap collision and an offset collision of an automobile. The front side member is made by molding a member by a press molding and so on, and thereafter, closing a section of the member by a spot welding. Normally, the front side member is buckled to thereby absorb the impact energy. It is important to stabilize a buckling mode and to prevent a bent and a fracture in a middle thereof to improve the absorption of the impact energy.

It is necessary to optimize a spot welding interval, a nugget diameter, and welding conditions to stabilize the buckling mode of the structural member. Therefore, a method to find an optimum condition to stabilize the buckling mode by estimating a fracture limit at a spot welded portion from the spot welding interval, the nugget diameter, and the welding conditions has been studied (for example, refer to Patent Literatures 1 to 3).

CITATION LIST

Patent Literature

Patent Literature 1: Japanese Laid-open Patent Publication No. 2005-148053
Patent Literature 2: Japanese Laid-open Patent Publication No. 2005-315854
Patent Literature 3: Japanese Laid-open Patent Publication No. 2007-304005
Patent Literature 4: International Publication No. 2011/126057 Pamphlet

SUMMARY OF INVENTION

Technical Problem

However, it is impossible to determine a fracture mode which will occur among a load fracture, a moment fracture, a nugget interior fracture in accordance with properties and a load state at the spot welded portion according to fracture analyzing methods disclosed in Patent Literatures 1 to 3, and therefore, an analysis accuracy in a collision simulation is not necessarily high.

Therefore, the present applicant applies a fracture analyzing method which improves the fracture analyzing method and capable of determine the fracture mode which occurs among the load fracture, the moment fracture, the nugget interior fracture (refer to Patent Literature 4). According to this fracture analyzing method, fracture limit values of each of the fracture modes of the load fracture, the moment fracture, the nugget interior fracture are found based on a sheet thickness "t", a tensile strength TS, an elongation El, a chemical composition, a nugget diameter "d" of a welded portion, an adjacent welded portion, an effective width B of the spot welded portion determined by a distance with an edge or an edge line, and a cross sectional height H of a steel sheet which is spot welded by using a computer. When a state quantity of the spot welded portion reaches the fracture limit value of any of the fracture modes, it is evaluated to be fractured at the fracture mode.

In the fracture analyzing method disclosed in Patent Literature 4, there is a problem in which it takes a long time for preparation setting because it is necessary to input necessary information such as the sheet thickness "t", the effective width B of each steel sheet for all of the spot welded portions though there is an advantage in which the analysis accuracy in the collision simulation is high. There are normally several thousand spot welded portions in the vehicle body of the automobile, and therefore, it takes a long time to input the necessary information for all of the spot welded portions.

In particular, in the fracture analyzing method disclosed in Patent Literature 4, an analysis algorism presupposing that the number of steel sheets to be spot-welded is two is developed. Accordingly, it is impossible to accurately perform the fracture analysis of the spot welded portions which are spot welded by stacking three or more pieces of the steel sheets. Namely, it is the actual circumstance that a program capable of fracture analyzing a three-layer model as it is not enabled yet. Therefore, the spot welded portions where the three pieces of the steel sheets are stacked to be spot welded are found by a manual work from among the spot welded portions of the vehicle body, and input information is adjusted such that it is apparently two-layer at a stage of the preparation setting before the fracture analysis. For example, at a spot welded portion where a steel sheet A, a steel sheet B, and a steel sheet C are stacked in tree-ply, a value of a sheet thickness of the steel sheet A and a value in which sheet thicknesses of the steel sheet B and the steel sheet C are added are input for the fracture analysis of a connection part between the steel sheet A and the steel sheet B, and thereby, it is adjusted to be apparently the two-layer spot welded portion. A lot of labor is necessary for works of the preparation setting as stated above.

Namely, various fracture analyzing methods have conventionally been proposed, but when the fracture analysis is actually performed, for example, a CAD data in which components, spot welded portions, and so on of a vehicle body are described as coordinates is used. When the fracture analysis is performed, an operator sets a CAD data into a model which can be recognized in a space as illustrated in FIG. 4 by using a CAD software, then the model is expanded or cut, and thereby, it is manually distinguished whether or not it is the three-layer spot welded portion from a relationship of other spot welded portions at a periphery relative to one spot welded portion. However, when the total number of spot welded portions is several thousand pieces or more and the number of components is a lot, it takes for several dozen days to mark the three-layer spot welded portions as for all of the spot welded portions.

The present invention is made in consideration of the problems as stated above, and an object thereof is to accurately determine the spot welded portions where at least three pieces of the components are stacked to be spot welded from among a lot of spot welded portions. Besides, another object of the present invention is to appropriately set the effective width B.

Solution to Problem

An analyzing method of a spot welded portion according to the present invention includes: acquiring bar elements as the spot welded portion; extracting other bar elements existing at a periphery of a target bar element which is targeted among the acquired bar elements; determining whether or not there is a bar element which shares the same end point with the target bar element among the extracted bar elements; determining that the target bar element and the bar element which shares the same end point with the target bar element are a three-layer spot welded portion when it is determined that there is the bar element which shares the same end point with the target bar element; and determining whether or not there is a bar element whose distance between elements with the target bar element is within a predetermined distance among the extracted bar elements when it is determined that there is not the bar element which shares the same end point with the target bar element, and determining that the target bar element and the extracted bar element are not the three-layer spot welded portion when it is determined that there is not the bar element within the predetermined distance.

An analyzing program of a spot welded portion according to the present invention causes a computer to execute: acquiring bar elements as the spot welded portion; extracting other bar elements existing at a periphery of a target bar element which is targeted among the acquired bar elements; determining whether or not there is a bar element which shares the same end point with the target bar element among the extracted bar elements; determining that the target bar element and the bar element which shares the same end point with the target bar element are a three-layer spot welded portion when it is determined that there is the bar element which shares the same end point with the target bar element; and determining whether or not there is a bar element whose distance between elements with the target bar element is within a predetermined distance among the extracted bar elements when it is determined that there is not the bar element which shares the same end point with the target bar element, and determining that the target bar element and the extracted bar element are not the three-layer spot welded portion when it is determined that there is not the bar element within the predetermined distance.

A recording medium according to the present invention is a computer readable recording medium recording a program causing a computer to execute: acquiring bar elements as a spot welded portion; extracting other bar elements existing at a periphery of a target bar element which is targeted among the acquired bar elements; determining whether or not there is a bar element which shares the same end point with the target bar element among the extracted bar elements; determining that the target bar element and the bar element which shares the same end point with the target bar element are a three-layer spot welded portion when it is determined that there is the bar element which shares the same end point with the target bar element; and determining whether or not there is a bar element whose distance between elements with the target bar element is within a predetermined distance among the extracted bar elements when it is determined that there is not the bar element which shares the same end point with the target bar element, and determining that the target bar element and the extracted bar element are not the three-layer spot welded portion when it is determined that there is not the bar element within the predetermined distance.

An analyzing apparatus of a spot welded portion according to the present invention, includes: a bar element acquisition part which acquires bar elements as the spot welded portion; a bar element extraction part which extracts other bar elements existing at a periphery of a target bar element which is targeted among the acquired bar elements; a share determination part which determines whether or not there is a bar element which shares the same end point with the target bar element among the extracted bar elements; and a welding determination part which determines that the target bar element and the bar element which shares the same end point with the target bar element are a three-layer spot welded portion when it is determined that there is the bar element which shares the same end point with the target bar element, and determines whether or not there is a bar element whose distance between elements with the target bar element is within a predetermined distance among the extracted bar elements when it is determined that there is not the bar element which shares the same end point with the target bar element, and which determines that the target bar element and the extracted bar element are not the three-layer spot welded portion when it is determined that there is not the bar element within the predetermined distance.

Advantageous Effects of Invention

According to the present invention, it is possible to accurately determine a spot welded portion where at least three pieces of components are stacked to be spot welded from among a lot of spot welded portions. It is therefore possible to shorten works of a preparation setting and to improve accuracy of a fracture analysis.

Besides, according to the present invention, it is possible to set an appropriate effective width. Accordingly, it is possible to shorten the works of the preparation setting and to improve the accuracy of the fracture analysis.

BRIEF DESCRIPTION OF DRAWINGS

FIG. 4 is a view illustrating a part of a vehicle body which is modeled as an analysis object.

FIG. 5 is a view illustrating an example of a database of components.

FIG. 6 is a view illustrating an example of a database of shell element information.

FIG. 7 is a view illustrating an example of a database of node point information and end point information.

DESCRIPTION OF EMBODIMENTS

Hereinafter, an analyzing method of a spot welded portion according to a preferable embodiment of the present invention is described in detail with reference to the attached drawings. Note that the technical scope of the present invention is not limited to the embodiments described below.

Figure 1:
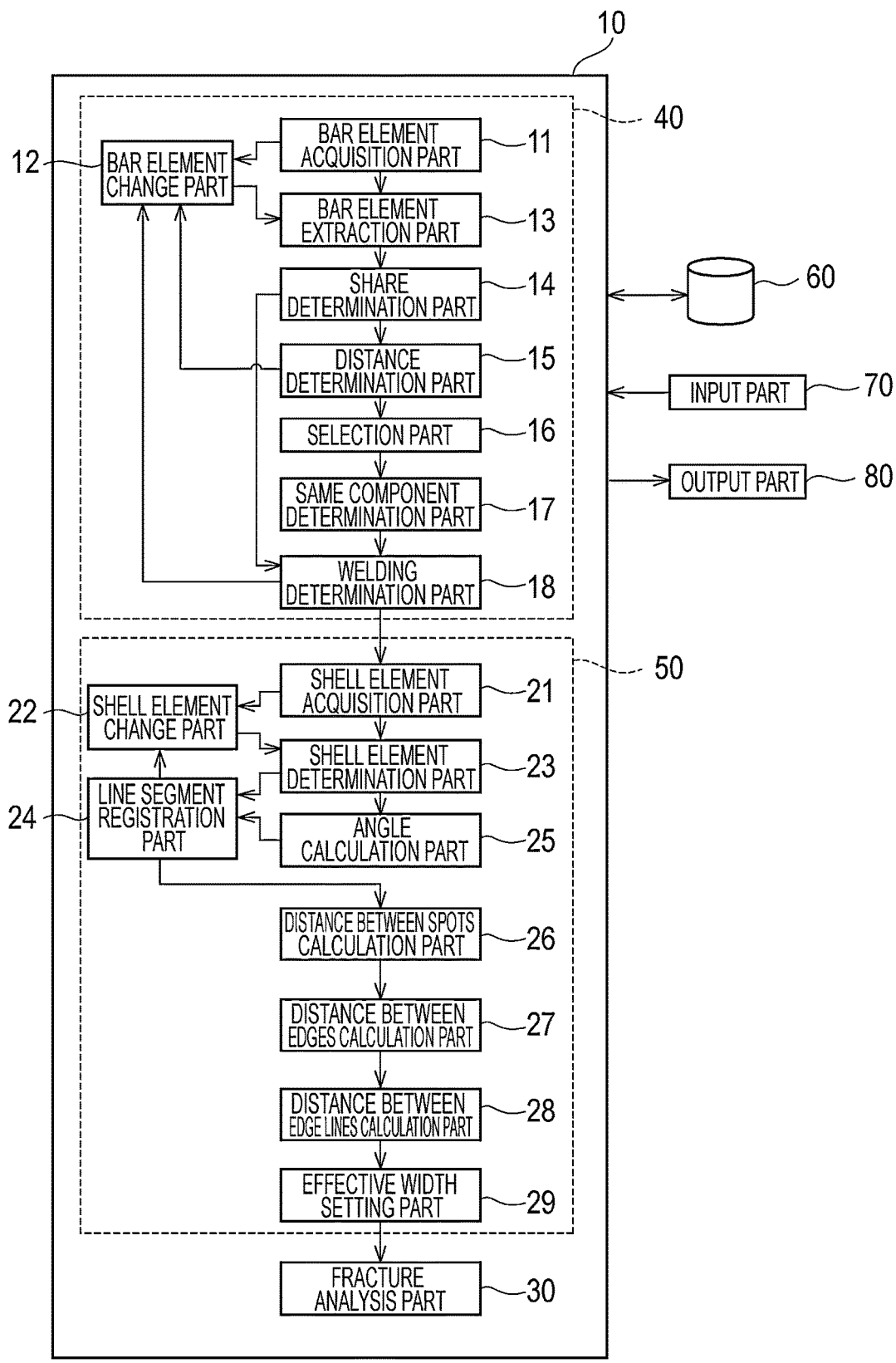
FIG. 1 is a view illustrating a functional configuration of an analyzing apparatus of a spot welded portion.

FIG. 1 is a view illustrating a functional configuration of an analyzing apparatus 10 of a spot welded portion (hereinafter referred to as the analyzing apparatus 10). The analyzing apparatus 10 has a welding determination unit 40, an effective width setting unit 50 and a fracture analysis part 30.

The welding determination unit 40 determines whether a spot welded portion being a model is a two-layer spot welded portion or a three-layer spot welded portion before the fracture analysis part 30 performs a fracture analysis of the spot welded portion. The fracture analysis part 30 performs the fracture analysis by using information determined by the welding determination unit 40, and thereby it becomes possible to improve accuracy of the fracture analysis. The welding determination unit 40 has a bar element acquisition part 11, a bar element change part 12, a bar element extraction part 13, a share determination part 14, a distance determination part 15, a selection part 16, a same component determination part 17, and a welding determination part 18. Note that processes performed at each part of the welding determination unit 40 are described later with reference to a flowchart in FIG. 10.

The effective width setting unit 50 sets an effective width of the spot welded portion being the model before the fracture analysis part 30 performs the fracture analysis of the spot welded portion. The fracture analysis part 30 performs the fracture analysis by using the effective width set at the effective width setting unit 50, and thereby, it is possible to improve the accuracy of the fracture analysis. The effective width setting unit 50 has a shell element acquisition part 21, a shell element change part 22, a shell element determination part 23, a line segment registration part 24, an angle calculation part 25, a distance between spots calculation part 26, a distance between edges calculation part 27, a distance between edge lines calculation part 28, and an effective width setting part 29. Note that processes performed at each part of the effective width setting unit 50 are described later with reference to a flowchart in FIG. 12.

Besides, a storage part 60, an input part 70, and an output part 80 are connected to the analyzing apparatus 10. The storage part 60 stores information of models, and database of each element constituting the models. The input part 70 inputs instructions and information to the analyzing apparatus 10 in accordance with operations of an operator. The output part 80 outputs an analysis result by the analyzing apparatus 10. Note that the storage part 60, the input part 70, and the output part 80 may be included in the analyzing apparatus 10.

At first, a model of an analysis object is described. The fracture analysis part 30 performs the fracture analysis on a computer by using the finite element method. Accordingly, the spot welded portion is modeled in advance by the operator by using bar elements (they are also called as beam elements), shell elements, solid elements, and so on. The fracture analysis part 30 performs the fracture analysis by applying values of a load loaded on each element as a vector state quantity and a moment.

Figure 2A:
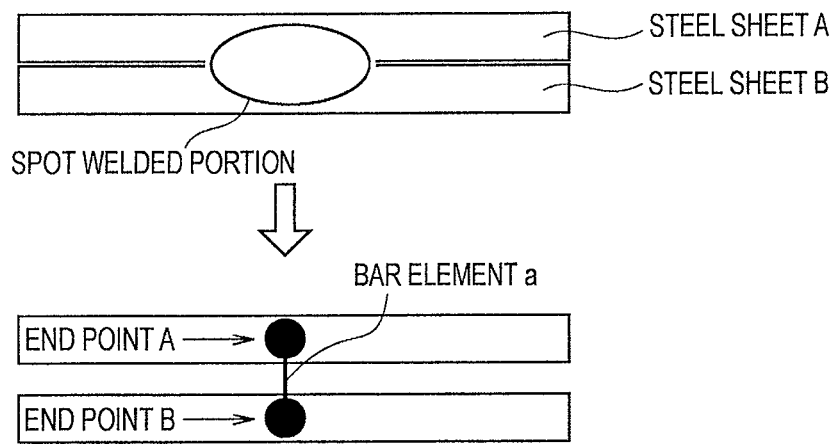
FIG. 2A is a view schematically illustrating a two-layer spot welded portion.

For example, a spot welded portion where two pieces of plate materials of a steel sheet A and a steel sheet B are stacked to be spot welded is imagined as a component. In this case, as it is schematically illustrated in FIG. 2A, a connection part between the steel sheet A and the steel sheet B is modeled by a bar element a, and end points A, B. On the other hand, the steel sheet A and the steel sheet B are modeled by the shell element. The fracture analysis part 30 calculates a stress, a shear force, and so on applied on the modeled bar element "a" and end points A, B, and performs the fracture analysis by determining whether or not they exceed fracture limit values.

Therefore, in the fracture analyzing method disclosed in Patent Literature 4, a sheet thickness "t", a tensile strength TS, an elongation El, a chemical composition, a nugget diameter "d" of a welded portion, an adjacent welded portion, an effective width B determined by a distance with an edge or an edge line, and a cross sectional height H of each steel sheet which is spot welded are input to the computer as necessary information.

Figure 2B:
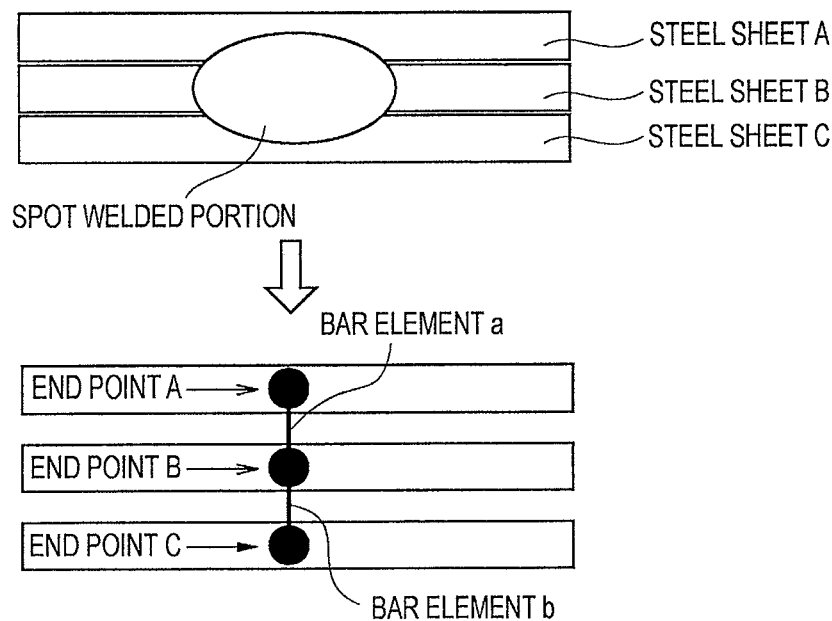
FIG. 2B is a view schematically illustrating a three-layer spot welded portion.

On the other hand, a spot welded portion where three pieces of plate materials of the steel sheet A, the steel sheet B, and a steel sheet C are stacked to be spot welded is imagined. In this case, the steel sheet A and the steel sheet B, the steel sheet B and the steel sheet C are modeled by the bar elements, and the end points as same as the case when they are two-layer. As a result, as it is schematically illustrated in FIG. 2B, it is modeled into a constitution in which the bar element "a" connecting between the steel sheet A and the steel sheet B, and a bar element "b" connecting between the steel sheet B and the steel sheet C are held, and an end point B on the steel sheet B is shared by the bar element "a" and the bar element "b".

However, in the fracture analyzing method disclosed in Patent Literature 4, it is impossible to perform the fracture analysis as a three-layer model as it is. Accordingly, the fracture analysis is performed after it is apparently adjusted to be a two-layer model. Specifically, when the bar element "a" connecting between the steel sheet A and the steel sheet B is focused, the steel sheet B and the steel sheet C are regarded as one element, and a value of a sheet thickness of the steel sheet A and a value in which sheet thicknesses of the steel sheet B and the steel sheet C are added are each input. On the other hand, when the bar element "b" connecting between the steel sheet C and the steel sheet B is focused, the steel sheet A and the steel sheet B are regarded as one element, and a value of the sheet thickness of the steel sheet C and a value in which the sheet thicknesses of the steel sheet A and the steel sheet B are added are each input. The adjustment as stated above is necessary, and therefore, it is necessary to develop an algorism to accurately determine the three-layer spot welded portions on the computer from among a lot of spot welded portions existing at the analysis object.

Note that when the operator models the three-layer and two-layer spot welded portions on the computer, they become models as illustrated in examples in FIG. 3A to FIG. 3F.

Figure 3A:
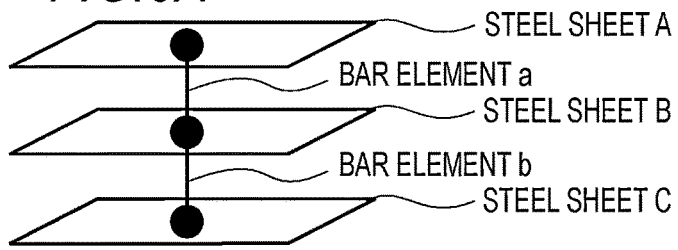
FIG. 3A is a view schematically illustrating the three-layer spot welded portion.

The model in FIG. 3A is the example which is accurately modeled into the three-layer spot welded portion.

Figure 3B:
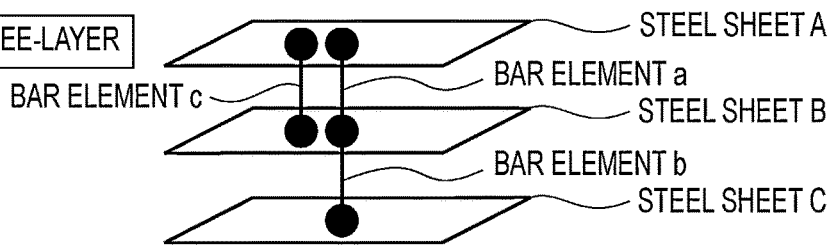
FIG. 3B is a view schematically illustrating the three-layer spot welded portion.
Figure 3C:
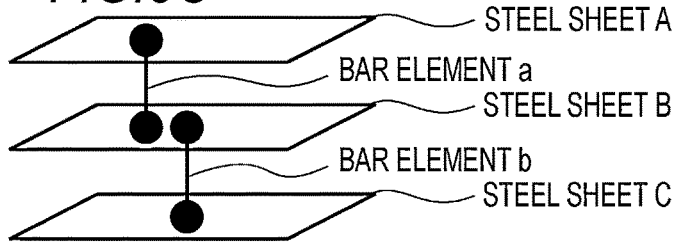
FIG. 3C is a view schematically illustrating the three-layer spot welded portion.

The model in FIG. 3C is the example which is modeled as different two-layer spot welded portions though it is actually the three-layer spot welded portion because a coordinate of an end point on the steel sheet B of the bar element "a" does not match with a coordinate of an end point on the steel sheet B of the bar element "b". There is a case when the three-layer spot welded portion is modeled into a mode such as the model in FIG. 3C depending on a software used to perform the modeling or an artificial reason.

The model in FIG. 3B is the model of a mode in which the three-layer spot welded portion and the two-layer spot welded portion are adjacent.

To improve the accuracy of the fracture analysis, it is necessary to accurately determine that the model in FIG. 3A, the model in FIG. 3B, and the model in FIG. 3C are each the three-layer spot welded portion. However, there is a case when the model in FIG. 3B and the model in FIG. 3C are misunderstood as the two-layer spot welded portions. The analyzing apparatus 10 of the embodiment is able to determine not only the model in FIG. 3A but also the model in FIG. 3B and the model in FIG. 3C as the three-layer spot welded portions by the later-described flowchart illustrated in FIG. 10.

Figure 3D:
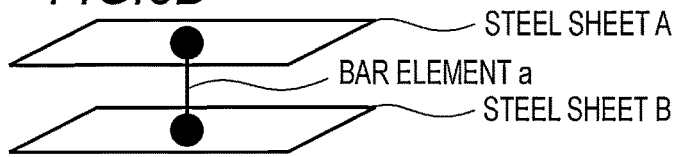
FIG. 3D is a view schematically illustrating the two-layer spot welded portion.

On the other hand, the model in FIG. 3D is the example which is accurately modeled into the two-layer spot welded portion.

Figure 3E:
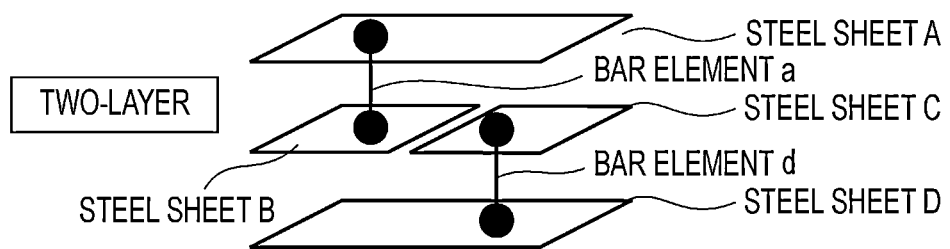
FIG. 3E is a view schematically illustrating the two-layer spot welded portion.
Figure 3F:
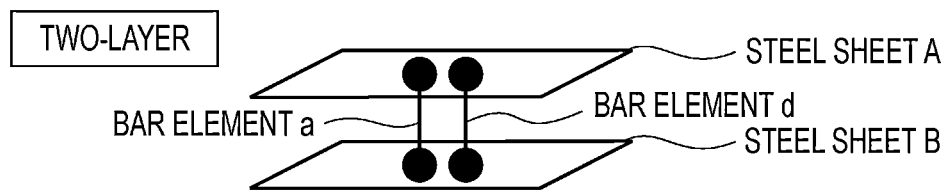
FIG. 3F is a view schematically illustrating the two-layer spot welded portion.

The model in FIG. 3E resembles to the mode of the model in FIG. 3C, and it is the model in which the number of intermediate steel sheets is two pieces, and separate steel sheets are each spot-welded in two-layer by the bar element "a" and a bar element The model in FIG. 3F is the model in which common steel sheets are spot welded in two-layer by two adjacent bar element "a" and bar element "d".

There is a case when the model in FIG. 3E and the model in FIG. 3F are misunderstood to be three-layer spot welded portions though they are two-layer spot welded portions. The analyzing apparatus 10 of the embodiment is able to determine that the model in FIG. 3E and the model in FIG. 3F are the two-layer spot welded portions by the later-described flowchart illustrated in FIG. 10.

For example, when the analysis object is a vehicle body of an automobile, the operator models the object by using the CAD software as, for example, schematically illustrated in FIG. 4. FIG. 4 is a view illustrating the vehicle body which is modeled as the analysis object, a front side member before deformation, and the front side member after deformation.

Information of each modeled shell element is stored at the storage part 60. An identification number (component number) to which each shell element belongs and a coordinate (x, y, z) of a node point of each shell element are included in the information of the shell element.

Besides, information of each modeled bar element is stored at the storage part 60 as the information of each spot welded portion. An identification number of each bar element (element number), coordinates (x, y, z) of end points of the bar element, and a representative point of the bar element are included in the information of the bar element.

Figures 8, 9:
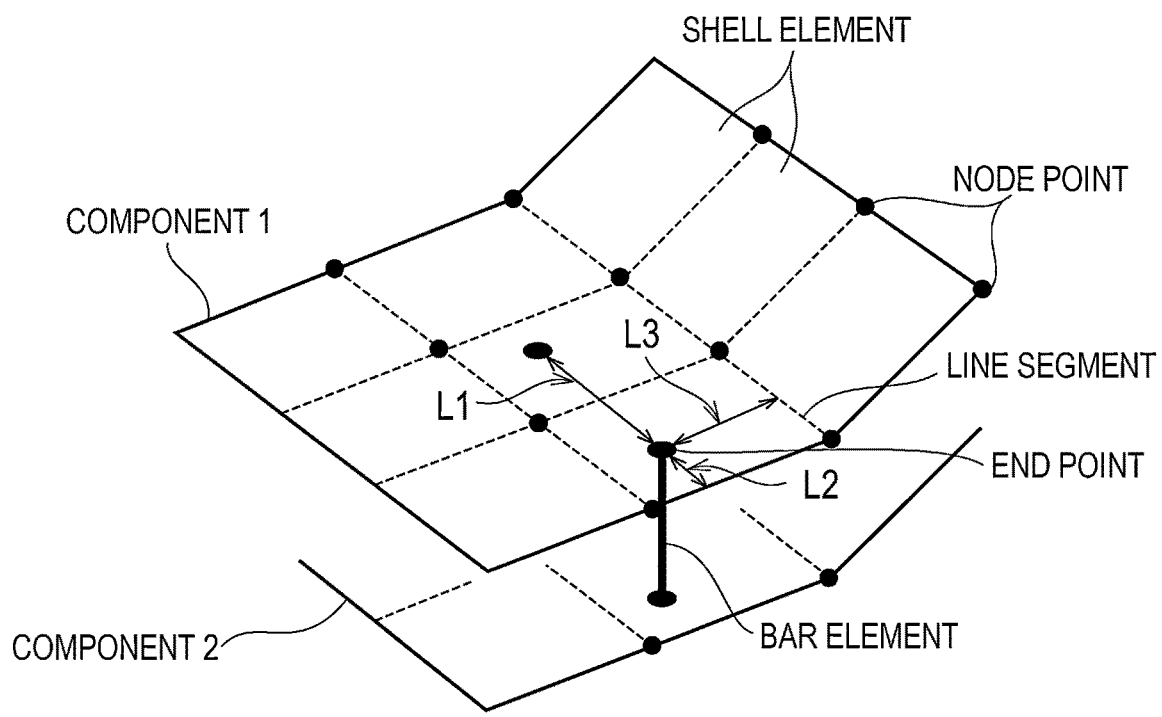
FIG. 8 is a view illustrating an example of a database of bar element information.
FIG. 9 is a view illustrating an example of a model.

FIG. 5 to FIG. 8 are views each illustrating an example of a database of information of each modeled element. The databases in FIG. 5 to FIG. 8 are stored at the storage part 60. FIG. 5 is the database of components, and for example, it is created and constituted by the operator. FIG. 6 is the database of shell element information. FIG. 7 is the database of node point information and end point information. FIG. 8 is the database of bar element information. The databases in FIG. 6 to FIG. 8 are constituted by using, for example, software from the CAD data of the model. Besides, FIG. 9 is a view illustrating an example of a model in which a part of the analysis object is modeled.

The database of the components illustrated in FIG. 5 exists for the number as same as the number of components of the model. For example, the steel sheet and so on are included in the components.

The identification number (component number) assigned to each component, base material information of the component are included in the database of the components. Information of a base material number and a cross sectional information number are included in the base material information.

Besides, a database of the cross sectional information is constituted in association with each cross sectional information number. The sheet thickness "t" of the component is included in the cross sectional information. Accordingly, the analyzing apparatus 10 is able to acquire the sheet thickness "t" of the component by referring to the database of the component. Note that information of ELFORM: Element formulation options, SHRF: Shear correction factor, NIP: Number of through thickness integration points, PROPT: Printout option, QR/IRID: Quadrature rule or Integration rule ID, ICOMP: Flag for orthotropic/anisotropic layered composite material model, SETYP: 2D solid element type, NLOC: Location of reference surface for three dimensional shell elements, MAREA: Non-structural mass per unit area, IDOF: Treatment of through thickness strain, EDGSET: Edge node set required for shell type seatbelts are also included in the cross sectional information as the information other than the sheet thickness "t" though they are not used in the embodiment.

Besides, a database (not-illustrated) of the base material information which is associated with the base material number is constituted. Accordingly, the analyzing apparatus 10 is able to acquire the base material information (for example, a chemical composition and so on) of the component by referring to the database of the base material information.

In the database of the shell element information illustrated in FIG. 6, information of an identification number (element number) assigned to each shell element, a component number to which each shell element belongs, an identification number of a node point (node point number) of each shell element are included. FIG. 6 is an example of the database of the shell element in which the component is set to be a square mesh. Therefore, one shell element has four node points (n1 to n4). When the component is set to be a triangle mesh, one shell element has three node points (n1 to n3). Information of coordinates (x, y, z) of the node points (n1 to n4) are stored at the database of the node point information in FIG. 7 in association with the node point number.

In the database of the bar element information illustrated in FIG. 8, information of an identification number assigned to each bar element (element number), an identification number of both end points (n1, n2) of each bar element (end point number), an identification number of a representative point (representative point number) are included. Information of the coordinates (x, y, z) of the both end points (n1, n2) are stored at the database of the end point information illustrated in FIG. 7 in association with the end point number. The representative point is, for example, a center point in a length direction of the bar element. The representative point is able to be set as a coordinate calculated from the coordinates (x, y, z) of the both end points of the bar element. The information of the coordinate (x, y, z) of the representative point is stored at a database (not-illustrated) of representative point information having a similar constitution as the database of the end point information in FIG. 7.

(Determination Process of Spot Welded Portion)

Subsequently, a process determining the two-layer spot welded portion and the three-layer spot welded portion is described with reference to the flowchart in FIG. 10. This process is executed by the welding determination unit 40 of the analyzing apparatus 10 in accordance with the instruction by the operator via the input part 70. Note that, here, the steel sheet is described as a component.

At first, at step S100, the bar element acquisition part 11 acquires information of the bar elements existing at the analysis object. Specifically, the bar element acquisition part 11 acquires the information of the bar elements from the database (FIG. 8) of the bar element information.

At step S101, the bar element acquisition part 11 acquires the end points of the bar element by each component. Specifically, the bar element acquisition part 11 acquires the end point numbers of the bar element from the database (FIG. 8) of the bar element information, and acquires the coordinate of the end point number from the database (FIG. 7) of the end point information. The bar element acquisition part 11 acquires the shell element containing the acquired coordinate from the database (FIG. 6) of the shell element information and the database (FIG. 7) of the node point information. The bar element acquisition part 11 acquires the component number of the component to which the shell element belongs from the database (FIG. 6) of the shell element. The bar element acquisition part 11 performs this process by each end point of the bar element, and thereby, it is possible to acquire the end points of the bar element by each component. The bar element acquisition part 11 stores information in which the bar element and the end points (including the end point numbers and the coordinates) of the bar element are associated by each component to a database (not-illustrated).

At step S102, the bar element change part 12 determines a target bar element which is to be targeted from among the acquired bar elements. Subsequently, the bar element extraction part 13 extracts other bar elements which exist at a periphery of the target bar element. Here, the bar element extraction part 13 extracts other bar elements each having an end point within a predetermined distance A from an end point of the target bar element. Specifically, the bar element extraction part 13 acquires a coordinate of the end point of the target bar element from the database (FIG. 8) of the bar element information and the database (FIG. 7) of the end point information. The bar element extraction part 13 extracts an end point number having a coordinate which is the predetermined distance or less from the acquired coordinate of the end point from the database (FIG. 7) of the end point information. The bar element extraction part 13 extracts element numbers having the extracted end point numbers from the database (FIG. 8) of the bar element information to thereby extracts other bar elements existing at the periphery of the target bar element.

For example, the target bar element is set to be the bar element "a", then the bar element "b" is extracted as the other bar element in case of the models in FIG. 3A and FIG. 3C. Besides, in case of the model in FIG. 3B, the bar element "b" and the bar element "c" are extracted. Besides, in case of the models in FIG. 3E and FIG. 3F, the bar element "d" is extracted.

On the other hand, in case of the model in FIG. 3D, other bar elements are not extracted. The welding determination part 18 is able to determine that the target bar element where other bar elements are not extracted as the two-layer spot welded portion.

Note that at the step S102, the bar element extraction part 13 may extract other bar elements each having a representative point within a predetermined distance from a representative point of the target bar element.

Next, at step S103, the share determination part 14 determines whether or not there is the bar element which shares the same end point with the target bar element among the extracted other bar elements. Specifically, the share determination part 14 refers to the database (FIG. 8) of the bar element information, compares the end point number of the target bar element and the end point numbers of other bar elements to thereby determine whether or not the same end point is shared. When the bar elements having different element numbers each have the end point having the same end point number, these bar elements share the same end point.

For example, when the target bar element is set to be the bar element "a", in case of the models in FIG. 3A and FIG. 3B, the bar element "a" and the bar element "b" share the end point on the component B, and it is determined that there is the bar element which shares the same end point. On the other hand, in case of the models in FIG. 3C, FIG. 3E, FIG. 3F, it is determined that there is not the bar element which shares the same end point.

When there is not the bar element which shares the same end point, the process proceeds to step S105, and when there is the bar element which shares the same end point, the process proceeds to step S104.

At the step S104, the welding determination part 18 determines that the target bar element and the bar element which shares the same end point with the target bar element are the three-layer spot welded portion where the components are stacked for three pieces. Here, the models in FIG. 3A and FIG. 3B are determined to be the three-layer spot welded portions from among a lot of spot welded portions of the analysis object.

At the step S105, the distance determination part 15 determines whether or not there is the bar element whose distance with the target bar element (a distance between elements) is within a predetermined distance B among other bar elements extracted at the step S102. Here, the predetermined distance is a distance shorter than the above-stated predetermined distance A, and for example, it is the sheet thickness, the nugget diameter, and so on.

Here, the distance determination part 15 calculates the distance between the end point of the target bar element and the end points of other bar elements by using the database (FIG. 8) of the bar element information and the database (FIG. 7) of the end point information, and determines whether or not there is one which is the sheet thickness of the component or less among the calculated distances. For example, when the target bar element is set to be the bar element "a", in case of the model in FIG. 3C, the sheet thickness means a sheet thickness of the component (the steel sheet B) which is in closest proximity to the bar element "b" and where the end point of the target bar element "a" is included. In case of the model in FIG. 3E, the sheet thickness means a sheet thickness of the component (the steel sheet B) which is in closest proximity to the bar element "d" and where the end point of the target bar element "a" is included. In case of the model in FIG. 3F, the sheet thickness means a sheet thickness of the component (the steel sheet A or the steel sheet B) which is in closest proximity to the bar element "d" and where the end point of the target bar element "a" is included. The distance determination part 15 specifies the component where the end point of the target bar element is included based on the information where the bar element and the end points of the bar element are associated by each component at the step S101, and is able to acquire the sheet thickness of the specified component from the database (FIG. 5) of the component.

Here, a reason why the sheet thickness, the nugget diameter, or the like is used as the predetermined distance B such as in the step S105 is because it is physically difficult to separately perform the spot-welding at a distance of the sheet thickness or less or the nugget diameter or less, and there is a case when it can be determined that it is the three-layer spot welded portion when the distance is the sheet thickness or less or the nugget diameter or less. Note that a distance between the representative point of the target bar element and the representative points of other bar elements may be used as the distance between elements at the step S105.

At the step S105, when there are other bar elements within the predetermined distance B, the process proceeds to step S108. Here, the model whose distance between elements is the predetermined distance B or less proceeds to the process at the step S108 among the models in FIG. 3C, FIG. 3E, and FIG. 3F. On the other hand, when there are not other bar elements within the predetermined distance B, the process proceeds to step S106. At the step S106, the welding determination part 18 determines that the target bar element and other bar elements which are extracted at the step S102 are separate spot welded portions, and they are not the three-layer spot welded portion. Here, it is determined that the model whose distance between elements is longer than the predetermined distance B is not the three-layer spot welded portion among the models in FIG. 3C, FIG. 3E, and FIG. 3F. Next, at step S107, the bar element change part 12 changes the target bar element, and thereby, the processes after the step S102 are performed again.

At the step S108, when there are a plurality of bar elements which are determined that each distance between elements is the predetermined distance B or less at the step S105, the selection part 16 selects the bar element whose distance between elements is the shortest among the plurality of bar elements as an object bar element. Note that when the number of bar elements whose distance between elements is determined to be the predetermined distance B or less is one, the selection part 16 selects the bar element as the object bar element.

At step S109, the same component determination part 17 determines whether or not the target bar element and the object bar element weld at least one same component. Specifically, the same component determination part 17 determines whether or not at least one of each component where the end points of the target bar element are included and each component where the end points of the object bar element are included are the same. The same component determination part 17 acquires the component numbers of the components where the end points of the target bar element and the object bar element are included by the method similar to the step S101, then compares the acquired component numbers, and thereby, it is possible to determine whether the target bar element and the object bar element weld at least the same component.

For example, the target bar element is set to be the bar element "a", and the object bar element is set to be the bar element "d", then in case of the model in FIG. 3E, it is determined that the same component is not welded. When the target bar element and the object bar element do not weld the same component and weld the components different from one another, the process proceeds to step S110.

At the step S110, the welding determination part 18 determines that the target bar element and the object bar element are separate spot welded portions, and the target bar element is the two-layer spot welded portion. Accordingly, for example, when the target bar element is set to be the bar element "a" and the object bar element is set to be the bar element "d", in case of the model in FIG. 3E, it is determined that it is the spot welded portion where the target bar element and the object bar element each spot weld the different components, and the target bar element is the two-layer spot welded portion. Namely, it is possible to prevent that the model in FIG. 3E is misunderstood to be the three-layer spot welded portion.

On the other hand, at the step S109, for example, when the target bar element is set to be the bar element "a" and the object bar element is set to be the bar element "b", in case of the model in FIG. 3C, it is determined that at least the same component (the steel sheet B) is welded. Besides, when the target bar element is set to be the bar element "a" and the object bar element is set to be the bar element "d", in case of the model in FIG. 3F, it is determined that the target bar element and the object bar element weld at least the same components (the steel sheet A, the steel sheet B). When the target bar element and the object bar element weld at least one same component, the process proceeds to step S111.

At the step S111, the same component determination part 17 determines whether or not the object bar element and the target bar element each weld the same components. Specifically, the same component determination part 17 determines whether or not both of each component where the end points of the object bar element are included and each component where the end points of the target bar element are included are the same. The same component determination part 17 acquires the component numbers of the components where the end points of the target bar element and the object bar element are included by the method similar to the step S101, then the acquired component numbers are compared, and thereby, it is possible to determine whether the target bar element and the object bar element each weld the same components.

For example, when the target bar element is set to be the bar element "a", and the object bar element is set to be the bar element "b", in case of the model in FIG. 3C, it is determined that they weld the same component (the steel sheet B), but do not each weld the same components. When the target bar element and the object bar element do not each weld the same component, the process proceeds to step S104.

At the step S104, the welding determination part 18 determines that the target bar element and the object bar element are the three-layer spot welded portion where the three pieces of the components are stacked to be spot welded. Accordingly, the model in FIG. 3C is determined to be the three-layer spot welded portion. Namely, it is possible to prevent that the model in FIG. 3C is misunderstood to be the two-layer spot welded portion.

On the other hand, at the step S111, for example, when the target bar element is set to be the bar element "a" and the object bar element is set to be the bar element "d", in case of the model in FIG. 3F, it is determined that the target bar element and the object bar element each weld the same components (the steel sheet A and the steel sheet B). When the target bar element and the object bar element each weld the same components, the process proceeds to the step S110.

At the step S110, the welding determination part 18 determines that it is the two-layer spot welded portion where the target bar element and the object bar element each spot-weld the same components. Accordingly, the model in FIG. 3F is determined to be the two-layer spot welded portion.

After that, at step S112, the bar element change part 12 determines whether or not the process finishes as for all of the bar elements. When the determination is not finished, the process returns to the step S107, and the target bar element is changed. On the other hand, when the determination is finished, the process proceeds to step S113, and the effective width setting unit 50 performs a setting process of the effective width. The process at the step S113 is described later with reference to the flowchart in FIG. 12.

At step S114, the fracture analysis part 30 performs the fracture analysis of the spot welded portion. Here, the fracture analysis part 30 performs the fracture analysis after the model is apparently adjusted such that the three-layer spot welded portion which is determined by the steps S100 to S112 is to be the two-layer spot welded portion. For example, at the spot welded portion where the steel sheet A, the steel sheet B, and the steel sheet C are spot welded by stacking three pieces, the fracture analysis is performed by adjusting such that it is the two-layer spot welded portion between the steel sheet A and a steel sheet where the steel sheet B and the steel sheet C are stacked in the fracture analysis of a connection part between the steel sheet A and the steel sheet B. Besides, in the fracture analysis of a connection part between the steel sheet B and the steel sheet C, the fracture analysis is performed by adjusting such that it is the two-layer spot welded portion between a steel sheet where the steel sheet A and the steel sheet B are stacked, and the steel sheet C. It is thereby possible to improve the accuracy of the fracture analysis by processing as stated above.

Note that the fracture analysis part 30 finds fracture limit values of respective fracture modes of a load fracture, a moment fracture, and a nugget interior fracture based on a sheet thickness "t", a tensile strength TS, an elongation El, a chemical composition, a nugget diameter "d" of a welded portion, an adjacent welded portion, an effective width B which is defined by a distance with an edge or an edge line, and a cross sectional height H of each of the steel sheets which are spot-welded based on, for example, the fracture analyzing method of Patent Literature 4. The fracture analysis part 30 estimates that it fractures at the fracture mode when a state quantity of the spot welded portion reaches the fracture limit value of any of the above-stated fracture modes.

At that time, it is possible to improve the accuracy of the fracture analysis by properly setting the effective width B by the effective width setting unit 50 at the step S113. Hereinafter, the effective width B is described.

Figure 11A:
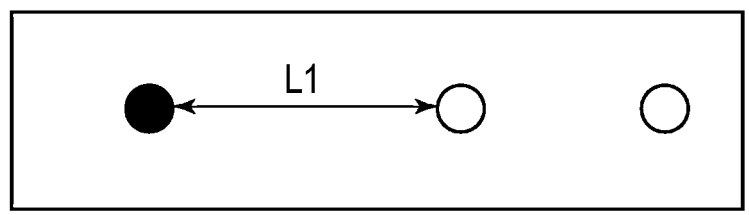
FIG. 11A is a view to explain a distance between spots L1.
Figure 11B:
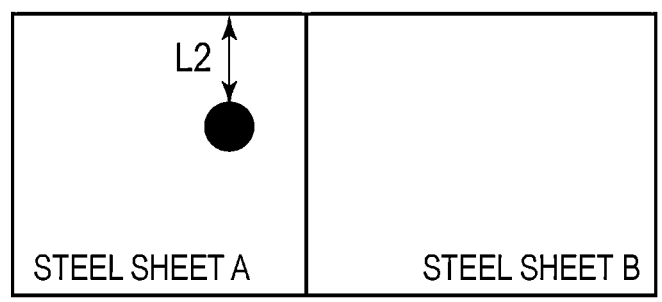
FIG. 11B is a view to explain a distance between edges L2.
Figure 11C:
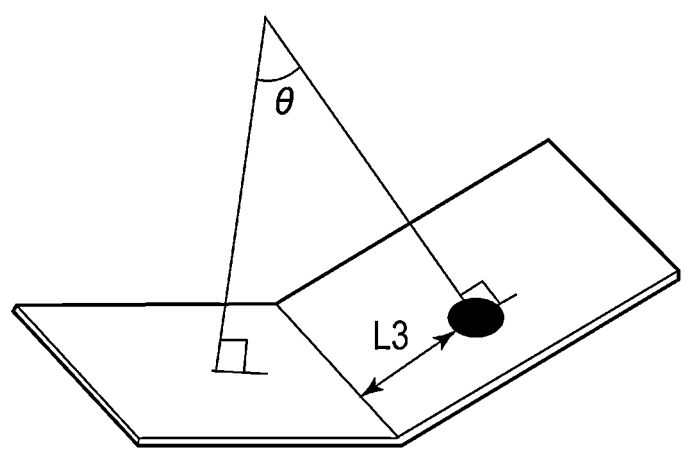
FIG. 11C is a view to explain a distance between edge lines L3.

As elements which can be the effective width B of the spot welded portion, there are three kinds as illustrated in FIG. 11A to FIG. 11C.

Firstly, when there are a plurality of spot welded portions on the same component, as it is schematically illustrated in FIG. 11A, a distance (a distance between spots) L1 to a spot welded portion which is the closest to a target spot welded portion is a candidate for the effective width B. When it is modeled into the shell element, a distance to the closest bar element existing on the same shell element becomes the distance between spots L1.

Secondly, as it is schematically illustrated in FIG. 11B, a value in which a distance (a distance between edges) L2 to the closest edge of a component (a welded component of the steel sheet A and the steel sheet B) which is welded by the target spot welded portion is doubled (=L2×2) becomes the candidate for the effective width B. Here, the distance between edges L2 is doubled because a value in which the distance between edges L2 is doubled can be supposed as a sheet width (effective width). The distance between edges L2 is doubled, and thereby, it is possible to set the effective width B at a proper value even when the spot welded portion is at a one-sided position on the component. Note that the edge means a line segment made up of two node points which belong to only one shell element.

Thirdly, as it is schematically illustrated in FIG. 11C, a value in which a distance (a distance between edge lines) L3 from the target spot welded portion to the closest edge line on the component which is welded by the spot welded portion is doubled (=L3×2) becomes the candidate for the effective width B. Here, the distance between edge lines L3 is doubled because it is possible to suppose the value in which the distance between edge lines L3 is doubled as a flange width (effective width) of the component. As stated above, the distance between edge lines L3 is doubled, and thereby, it is possible to set the effective width B at a proper value even when the spot welded portion is at a one-sided position on the component. Note that the edge line means an edge (a line segment made up of two node points) which is common to two shell elements and in which an angle θ formed by normal vectors of the shell elements is a threshold value or more.

In the setting process of the effective width at the step S113 of the embodiment, the effective width setting unit 50 calculates the three candidates for the effective width, and sets one of the calculated candidates as the effective width B. The process at the step S113 is described with reference to a flowchart in FIG. 12.

(Setting Process of Effective Width B)

At first, at step S200, the shell element acquisition part 21 acquires information of the shell elements existing at the analysis object. Specifically, the shell element acquisition part 21 acquires the information of the shell elements from the database (FIG. 6) of the shell element information.

At step S201, the shell element change part 22 decides one target shell element which is targeted from among the acquired shell elements. Subsequently, the shell element determination part 23 determines whether or not an adjacent shell element exists at a line segment of the target shell element. Specifically, the shell element determination part 23 determines whether or not there is the shell element whose two node point numbers are the same among four node point numbers of the target shell element with reference to the database (FIG. 6) of the shell element information. When there is the shell element whose two node point numbers are the same, it is determined that there is the adjacent shell element, and the process proceeds to step S203. On the other hand, when there is not the shell element whose two node point numbers are the same, it is determined that there is not the adjacent shell element, and the process proceeds to step S202. Note that when only one node point number of the shell element is the same, it is determined that the shell element is at a diagonal position with the target shell element and is not the adjacent shell element.

At the step S202, the line segment registration part 24 registers the line segment of the target shell element as an edge of the component to a database (not-illustrated).

At the step S203, the angle calculation part 25 calculates the angle θ formed by the normal vectors of the target shell element and the adjacent shell element. Specifically, the angle calculation part 25 is able to calculate the angle θ by using the database (FIG. 6) of the shell element information.

At step S204, the angle calculation part 25 determines whether or not the angle θ is a threshold value or more. Here, the threshold value can be arbitrary set within a range of 10 degrees to 15 degrees, and it is preferably 10 degrees. Note that when the threshold value is less than 10 degrees, there is a case when a curvature of the component is misunderstood to be the edge line, and there is a case when accuracy of extraction is lowered. On the other hand, when it exceeds 15 degrees, there is a case when leakage of extraction of the edge line occurs. When it is smaller than the threshold value, the process proceeds to step S206, and when it is the threshold value or more, the process proceeds to step S205.

At the step S205, the line segment registration part 24 registers a line segment which connects between the target shell element and the adjacent shell element as an edge line of the component (more specifically, a part of the edge line of the component) to a database (not-illustrated).

At the step S206, the shell element change part 22 determines whether or not the above-stated processes are finished as for all of the acquired shell elements. When the processes are not finished, the process returns to the step S201, and when the processes are finished, the process proceeds to step S207.

At the step S207, the distance between spots calculation part 26 sequentially decides one target bar element which is targeted from among the bar elements. Subsequently, the distance between spots calculation part 26 calculates a distance from the target bar element to the shortest bar element as the distance between spots L1. Specifically, the distance between spots calculation part 26 extracts the adjacent bar element which is adjacent to the target bar element by, for example, the process similar to the above-stated step S102. The distance between spots calculation part 26 determines whether or not there is the adjacent bar element existing on a common component with the target bar element among the adjacent bar elements based on, for example, the information in which the bar element and the end points of the bar element are associated by each component at the step S101. When there is the adjacent bar element existing on the component in common with the target bar element, the distance between spots calculation part 26 calculates the distance from the target bar element to the adjacent bar element which is in the shortest distance based on, for example, the information in which the bar element and the end points of the bar element are associated by each component at the step S101. Here, the distance from the target bar element to the adjacent bar element is, for example, a distance between the end points with each other on the common component. This distance is desirable to be a stroke distance along a plane of the component, but it may be an absolute distance at a three-dimensional space.

At the step S207, the distance between spots calculation part 26 calculates a distance between spots $L1_1$ of one target bar element, then calculates a distance between spots $L1_2$ of a next target bar element. The distance between spots calculation part 26 calculates distances between spots $L1_1$, $L1_2, \ldots, L1_n$ of all of the bar elements.

At step S208, the distance between edges calculation part 27 sequentially decides one target bar element which is targeted from among the bar elements. Subsequently, the distance between edges calculation part 27 calculates a distance from the target bar element to the shortest edge as a distance between edges $L2_1$. Specifically, the distance between edges calculation part 27 is able to set the shortest distance as a distance between edges L2 among the distances from the target bar element to each edge in the database registered at the step S202. Here, the distance from the target bar element to the edge is, for example, a distance from the end point of the target bar element to the line segment of the shell element which is determined to be the edge. This distance is desirable to be a stroke distance along a plane of the shell element, but it may be an absolute distance at a three-dimensional space.

At the step S208, the distance between edges calculation part 27 calculates the distance between edges $L2_1$ of one target bar element, then calculates a distance between edges $L2_2$ of a next target bar element. The distance between edges calculation part 27 calculates distances between edges $L2_1$, $L2_2, \ldots, L2_n$ of all of the bar elements.

At step S209, the distance between edge lines calculation part 28 sequentially decides one target bar element which is targeted from among the bar elements. Subsequently, the distance between edge lines calculation part 28 calculates a distance from the target bar element to the shortest edge line as a distance between edge lines $L3_1$. Specifically, the distance between edge lines calculation part 28 is able to set the shortest distance as a distance between edge lines L3 among the distances from the target bar element to each edge line in the database registered at the step S205. Here, the distance from the target bar element to the edge line is, for example, a distance from the end point of the target bar element to the line segment of the shell element which is determined to be the edge line. This distance is desirable to be a stroke distance along a plane of the shell element, but it may be an absolute distance at a three-dimensional space.

At the step S209, the distance between edge lines calculation part 28 calculates the distance between edge lines $L3_1$ of one target bar element, then calculates a distance between edge lines $L3_2$ of a next target bar element. The distance between edge lines calculation part 28 acquires information of distances between edge lines $L3_1, L3_2, \ldots, L3_n$ of all of the bar elements.

Note that the distance between spots $L1_1$, the distance between edges $L2_1$, and the distance between edge lines $L3_1$ are each a distance calculated for the same target bar element.

At step S210, the effective width setting part 29 compares the value of the distance between spots L1 calculated at the step S207, the value in which the distance between edges L2 calculated at the step S208 is doubled, and the value in which the distance between edge lines L3 calculated at the step S209 is doubled as for each bar element, and selects a minimum value (the shortest distance).

At step S211, the effective width setting part 29 sets the selected distance as the effective width B of the spot welded portion which is modeled by the bar element. Note that the effective width setting part 29 sets a value as the effective width B as long as the value is the minimum value even when all of or two of the value of the distance between spots L1, the value in which the distance between edges L2 is doubled, and the value in which the distance between edge lines L3 is doubled are the same value.

Next, the process of the fracture analysis by the fracture analysis part 30 is described.

Figure 12:
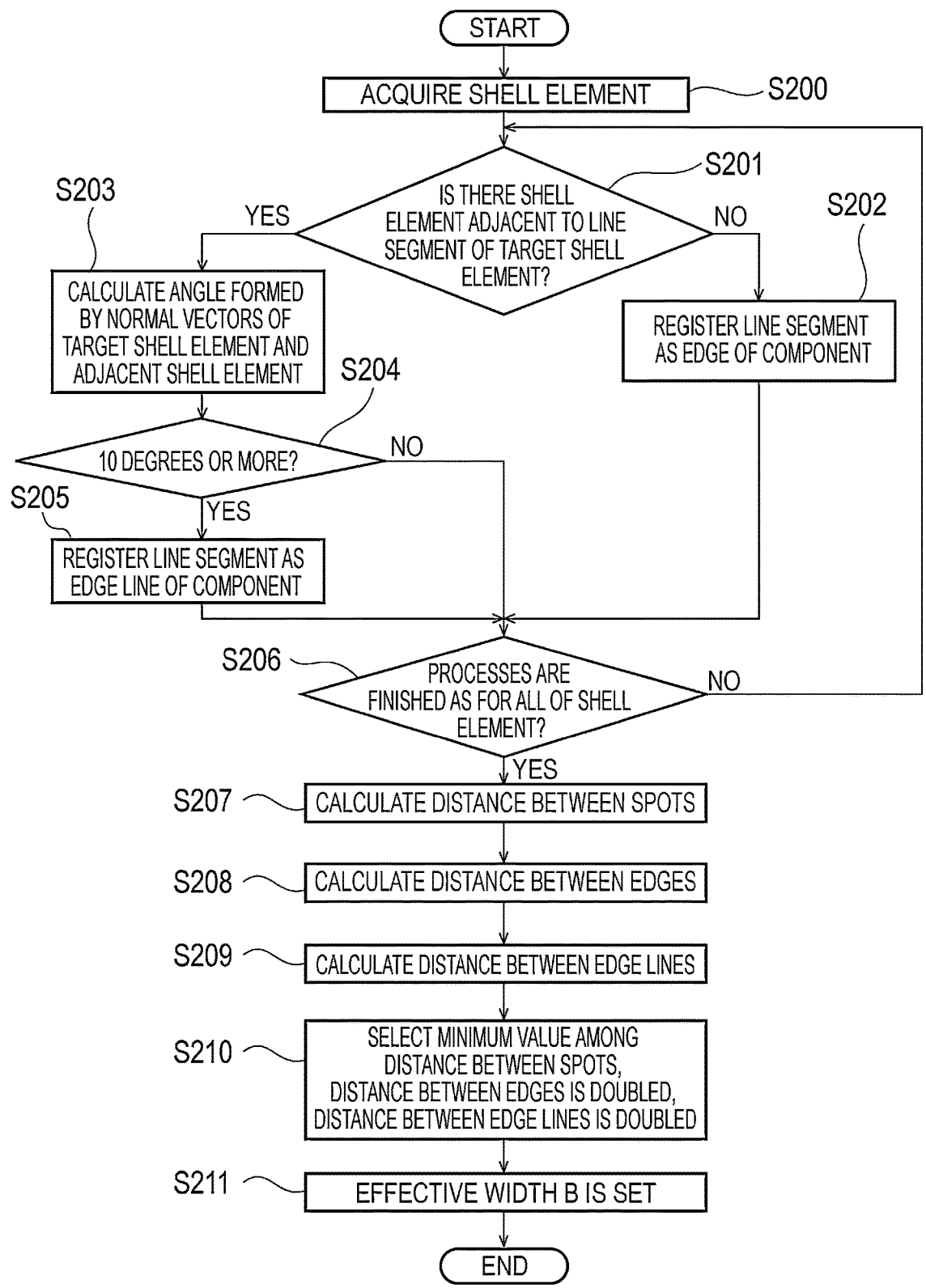
FIG. 12 is a flowchart illustrating a setting process of an effective width B.

In the following description, the fracture analyzing method in Patent Literature 4 is cited as an example, but it is not necessarily limited to this fracture analyzing method. The fracture analysis part 30 reads input information as a preparation setting before the fracture analysis is performed. The information of the three-layer spot welded portions which are determined by the flowchart in FIG. 10 and the information of the effective widths B which are set by the flowchart in FIG. 12 are included in the input information.

Here, input items when the steel sheet A, and the steel sheet B are spot-welded are illustrated in Table 1. As illustrated in Table 1, input items used for determination are different depending on the fracture modes. The fracture analysis part 30 is able to perform the fracture analysis for all of the fracture modes by using the input items illustrated in Table 1, and an operator is able to know the fracture mode which reaches the fracture limit value at the earliest.

TABLE 1

| | | | CRITERIA | | |
|---|---|---|---|---|---|
| INPUT ITEM | | | LOAD FRAC-TURE MODE | MOMENT FRAC-TURE MODE | NUGGET INTERIOR FRAC-TURE MODE |
| STEEL SHEET | STEEL SHEET A | SHEET THICKNESS | ○ | ○ | |
| | | TENSILE STRENGTH | ○ | ○ | |
| | | ELON-GATION | ○ | ○ | |
| | | COMPO-SITION | | | ○ |
| | STEEL SHEET B | SHEET THICKNESS | ○ | ○ | |
| | | TENSILE STRENGTH | ○ | ○ | |
| | | ELON-GATION | ○ | ○ | |
| | | COMPO-SITION | | | ○ |

TABLE 1-continued

| | | CRITERIA | | |
|---|---|---|---|---|
| INPUT ITEM | | LOAD FRAC-TURE MODE | MOMENT FRAC-TURE MODE | NUGGET INTERIOR FRAC-TURE MODE |
| WELDED PORTION SHAPE | NUGGET DIAMETER | ○ | ○ | ○ |
| | EFFECTIVE WIDTH | ○ | ○ | |
| | CROSS SECTIONAL HEIGHT | | ○ | |

The fracture analysis part 30 calculates the fracture limit value by using the input items each illustrated by a round mark in Table 1 in accordance with each fracture mode of the load fracture, the moment fracture, and the nugget interior fracture. Note that a calculation method of the fracture limit value at each fracture mode is not limited, but for example, it is preferable to use the following method.

At first, in case of the load fracture, a method is preferable in which the shear tensile test or the cross tensile test of a test piece having the spot welded portion is performed, a relationship between a ratio d/w between a nugget diameter "d" (mm) and a width W (mm) of the test piece, and a stress concentration coefficient α found by an expression (1) is found in advance, and a fracture limit load Fs (N) of the spot welded portion by the shear tensile test is calculated by an expression (2) while setting a material having an arbitrary tensile strength. Here, the effective width B which is set at the step S211 is applied for the width W of the test piece.

$$\alpha = TS \cdot W \cdot t / F \tag{1}$$

Here, TS: tensile strength (MPa), t: thickness of test piece (mm), F: fracture limit tension (N)

$$Fs = TS \cdot W \cdot t / \alpha \tag{2}$$

Besides, in case of the moment fracture, a method is preferable in which the flange tensile test having the spot welded portion is performed, a moment efficiency γ by an expression (3) is found in advance from a bending moment M (N·m) applied on an end part of the spot welded portion and a full plastic moment Mp (N·m) which can be theoretically found from a sheet thickness, a sheet width, and a strength property of a test material, and a fracture limit moment Mlim (N·m) of the spot welded portion by the flange tensile test by an expression (4) is calculated from the moment efficiency γ and a full plastic moment MP' for a material having an arbitrary sheet thickness, sheet width, and strength property. Here, the effective width B which is set at the step S211 is applied for the sheet width of the test material.

$$\gamma = Mp/M \tag{3}$$

$$Mlim = Mp'/\gamma \tag{4}$$

Besides, in case of the nugget interior fracture, for example, a method is preferable in which the fracture limit load Fs (N) of the spot welded portion is calculated by the following expression (5).

$$Fs = e \times \pi (d/2)^2 \times (f \times Ceq + g) \tag{5}$$

Here, d: nugget diameter (mm), Ceq: weighted average in thickness direction of nugget part carbon equivalent, e, f, g: coefficients The fracture analysis part 30 calculates a state variable by each fracture mode based on a load moment output of each element of the spot welded portion by each time.

The fracture analysis part 30 compares the fracture limit value and the state variable by each fracture mode. When the state variable of any of the fracture modes reaches the fracture limit value, the fracture analysis part 30 determines that the fracture already occurs after that, and lowers an allowable load value in accordance with a relative displacement (distortion) of an element of the spot welded portion after that.

The fracture analysis part 30 outputs fracture detailed information via the output part 80 after dynamic calculations of all processes are finished.

According to the embodiment, the target bar element and the bar element which shares the same end point with the target bar element are determined to be the three-layer spot welded portion among other bar elements existing at the periphery of the target bar element, and thereby, it is possible to automatically and accurately determine the spot welded portion where the components are spot-welded by stacking at least three pieces from among a lot of spot welded portions. Besides, when other bar elements which share the same end point with the target bar element do not exist, and further, other bar elements whose distances between elements with the target bar element are within the predetermined distance do not exist, it is determined that the target bar element and other bar elements are not the three-layer spot welded portion, and thereby, it is possible to prevent that, for example, the two-layer spot welded portion is misunderstood to be the three-layer spot welded portion. The information of the three-layer spot welded portion is used for the fracture analysis, and thereby, it is possible to improve the accuracy of the fracture analysis.

Further, according to the embodiment, the minimum value among the value of the distance between spots, the value in which the distance between edges is doubled, and the value in which the distance between edge lines is doubled is automatically set as the effective width B of the spot welded portion. The effective width B is used for the fracture analysis, and thereby, it is possible to improve the accuracy of the fracture analysis.

Conventionally, it takes for 10 minutes per one piece of spot welded portion for the determination of the three-layer spot welded portion and the setting of the effective width B by manual work. Accordingly, in a model where there are the total number of spot welded portions of 5000 pieces, it takes for 35 days as a total. On the other hand, when a program enabling the flowcharts in FIG. 10 and FIG. 12 is used such as the embodiment, the processes complete for a several minutes even if the model has the total number of spot welded portions of 5000 pieces, and it is possible to largely reduce a preparation setting time.

Figure 13:
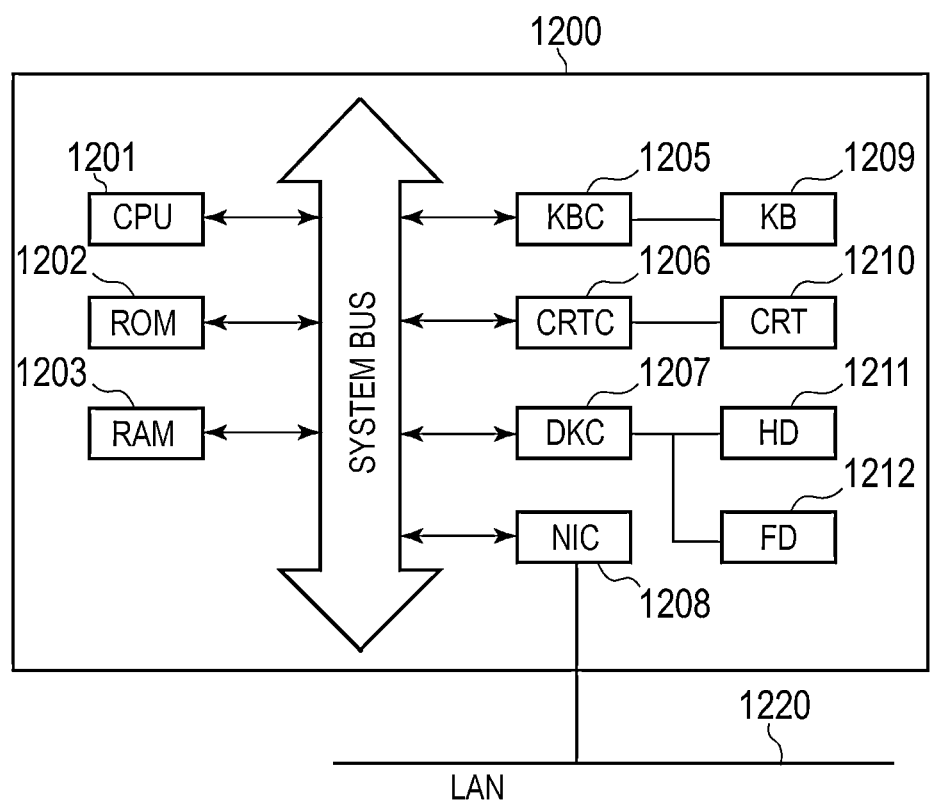
FIG. 13 is a view illustrating a configuration of an analyzing apparatus of a spot welded portion.

FIG. 13 is a schematic view illustrating an example of a hardware configuration of the analyzing apparatus 10. A reference numeral 1200 is a computer (PC) and it includes a CPU 1201. The CPU 1201 executes device control software stored at a ROM 1202 or a hard disk (HD) 1211, or supplied from a flexible disk drive (FD) 1212, to thereby totally control each device connected to a system bus. The CPU 1201 executes an analyzing program (program) stored at the ROM 1202 or the hard disk (HD) 1211, to thereby enable a functional configuration of the welding determination unit 40 and the effective width setting unit 50 of the analyzing apparatus 10 of the embodiment. Besides, the CPU 1201 executes a fracture analyzing program (program) stored at the ROM 1202 or the hard disk (HD) 1211, to thereby enable a functional configuration of the fracture analysis part 30 of the analyzing apparatus 10 of the embodiment. Note that in the embodiment, the analyzing program and the fracture analyzing program are separated, but it may be constituted by including the fracture analyzing program in the analyzing program.

A reference numeral 1203 is a RAM, and it functions as a main memory, a work area, and so on of the CPU 1201. A reference numeral 1205 is a keyboard controller (KBC), and it controls to input a signal input from a keyboard (KB) 1209 into the computer 1200. A reference numeral 1206 is a display controller (CRTC), and it controls a display on a display device (CRT) 1210. A reference numeral 1207 is a disk controller (DKC), and it controls accesses with the hard disk (HD) 1211 and the flexible disk (FD) 1212 which store a boot program, a plurality of applications, edit files, user files, a network control program, and so on. Here, the boot program is a startup program which starts execution (operation) of hardware and software of a personal computer.

A reference numeral 1208 is a network interface card (NIC), and it performs two-way exchange of data with a network printer, other network equipments, or other PCs via a LAN 1220.

Besides, means to supply programs to the computer, for example, a computer readable recording medium such as a CD-ROM recording programs or a transmission medium such as internet which transmits programs are also applied as the embodiment of the present invention. Besides, a program product such as the computer readable recording medium which records the programs is also applied as the embodiment of the present invention. The program, the recording medium, the transmission medium, and the program product are included in the scope of the present invention. As the recording medium, for example, a flexible disk, a hard disk, an optical disk, a magnetic-optical disk, a CD-ROM, a magnetic tape, a nonvolatile memory, a ROM, and so on can be used.

EXAMPLES

Next, examples performed to verify the effects of the present invention are described.

First Example

Figure 14A:
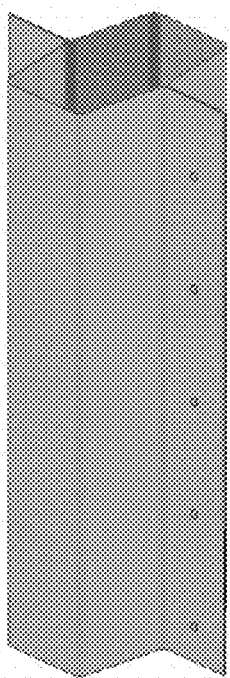
FIG. 14A is a view illustrating a model before deformation of a first example.
Figure 14B:
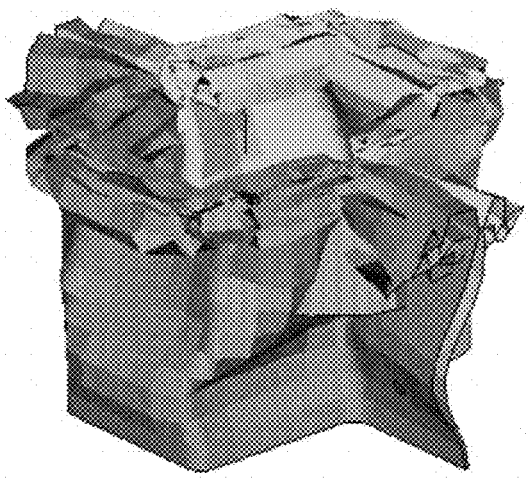
FIG. 14B is a view illustrating the model after deformation of the first example.

In a first example, the fracture analysis of models illustrated in FIG. 14A, FIG. 14B is described. FIG. 14A is a model before deformation which is constituted by a two-layer spot welded portion, and FIG. 14B is a model after deformation.

Conditions of the model are, steel type: JSC590Y, sheet thickness: 1.0 mm, member length: 500 mm, cross section: 50 mm×100 mm (except a flange), upper surface: a rigid wall of 500 kg is collided at an initial velocity of 10 m/s, lower surface: fixed. The spot welded portion has, the nugget diameter: 4 mm, the number of spot welded portions: 10 pieces (5 pieces in one side), pitch: 60 mm. As the fracture analyzing program, LS-DYNA (finite element analyzing program) is used.

Figure 15A:
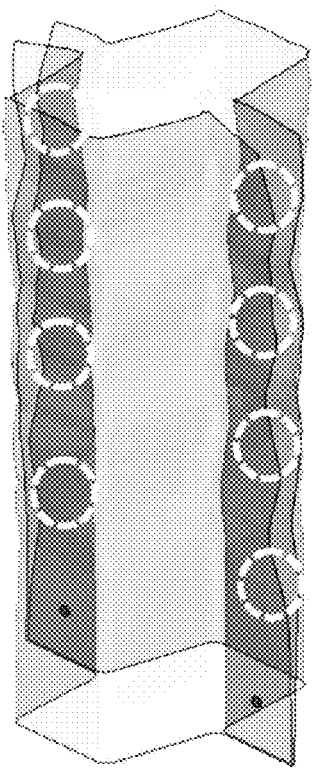
FIG. 15A is a view outputting an analysis result of an example 1A.

In an example 1A, the effective width B calculated by using the flowchart in FIG. 12 was set, then the fracture analysis part 30 performed the fracture analysis of the spot welded portion. FIG. 15A is a view where an analysis result of the example 1A is output.

Figure 15B:
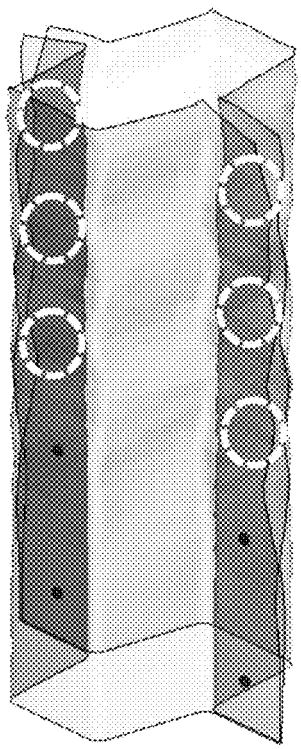
FIG. 15B is a view outputting an analysis result of a comparative example 1B.

In a comparative example 1B, a default value (40 mm) defined in advance was set as the effective width B, then the fracture analysis part 30 performed the fracture analysis of the spot welded portion. FIG. 15B is a view where an analysis result of the comparative example 1B is output.

Note that FIG. 15A and FIG. 15B illustrate analysis results when the deformation from FIG. 14A to FIG. 14B proceeded for 20%.

In the example 1A illustrated in FIG. 15A, the fractures occurred at eight pieces among 10 pieces of the spot welded portions, and it was the same number as the number of actually fractured portions. On the other hand, in the comparative example 1B illustrated in FIG. 15B, the fractures occurred at six pieces among 10 pieces of the spot welded portions, and it was different from the number of actually fractured portions.

As stated above, the effective width B is set by the flowchart illustrated in FIG. 12, and thereby, it is possible to improve the accuracy of the fracture analysis of a collision simulation in addition to largely reduce the time for the preparation setting. In particular, the effect becomes obvious as the number of spot welded portions increases to several hundred pieces, several thousand pieces.

Second Example

Figure 16A:
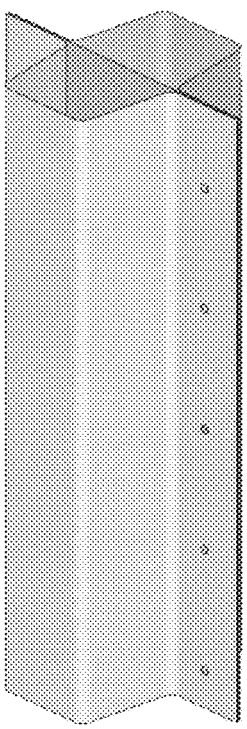
FIG. 16A is a view illustrating a model before deformation of a second example.
Figure 16B:
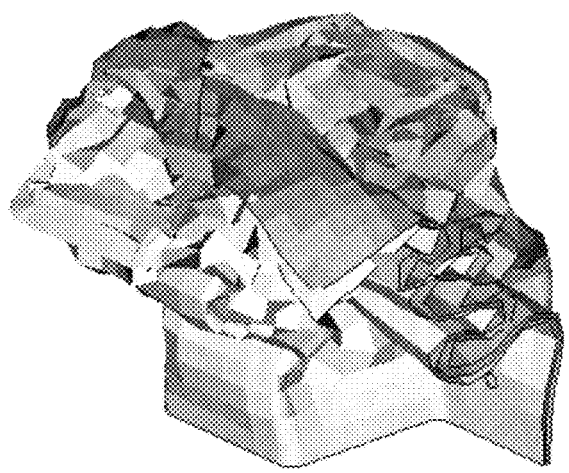
FIG. 16B is a view illustrating the model after deformation of the second example.

In a second example, the fracture analysis of models illustrated in FIG. 16A, FIG. 16B is described. FIG. 16A is a model before deformation which is constituted by a three-layer spot welded portion, and FIG. 16B is the model after deformation. Conditions of the models are the same as the conditions of the first example.

Figure 10:
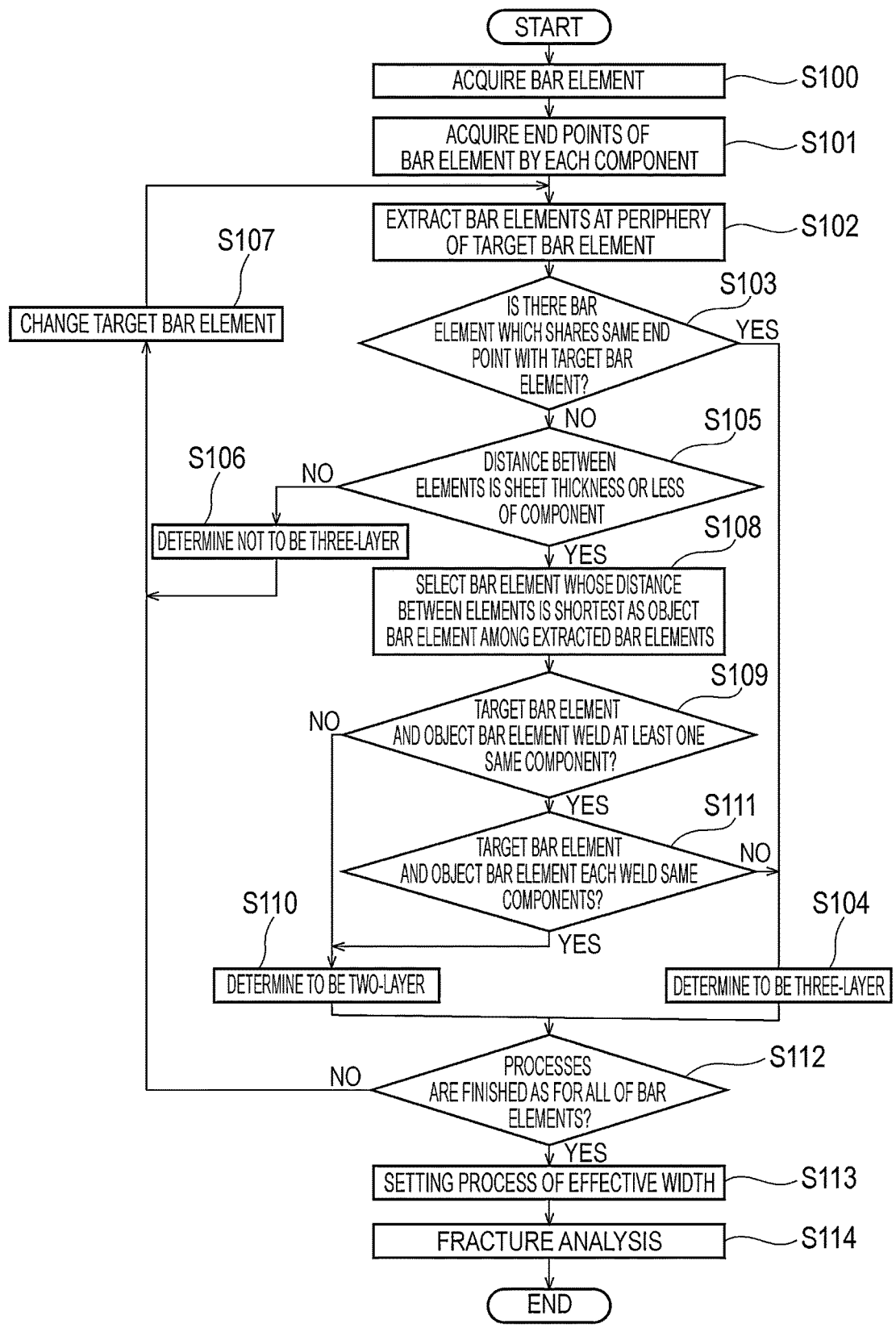
FIG. 10 is a flowchart illustrating a process determining the three-layer spot welded portion.
Figure 17A:
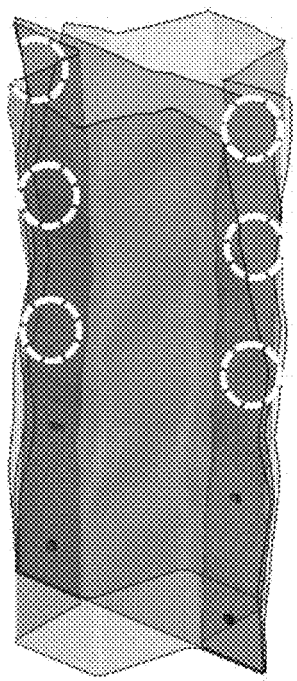
FIG. 17A is a view outputting an analysis result of an example 2A.

In an example 2A, the three-layer spot welded portion was determined by using the flowchart in FIG. 10, further the effective width B calculated by using the flowchart in FIG. 12 was set, then the fracture analysis part 30 performed the fracture analysis of the spot welded portion. FIG. 17A is a view where an analysis result of the example 2A is output.

Figure 17B:
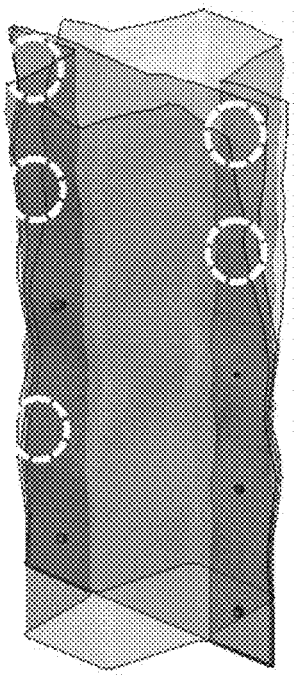
FIG. 17B is a view outputting an analysis result of an example 2B.

In an example 2B, the three-layer spot welded portion was determined by using the flowchart in FIG. 10, further a default value (40 mm) defined in advance was set as the effective width B, then the fracture analysis part 30 performed the fracture analysis of the spot welded portion. FIG. 17B is a view where an analysis result of the example 2B is output.

Figure 17C:
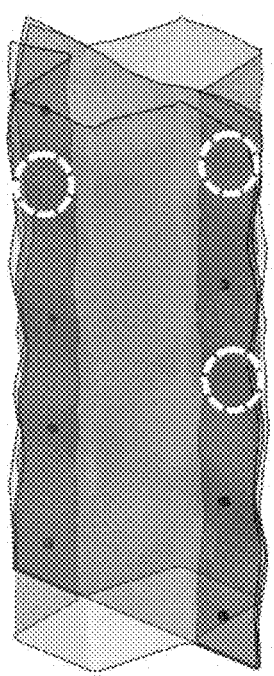
FIG. 17C is a view outputting an analysis result of a comparative example 2C.

In a comparative example 2C, the three-layer spot welded portion was not determined, the default value (40 mm) defined in advance was set as the effective width B, then the fracture analysis part 30 performed the fracture analysis of the spot welded portion. FIG. 17C is a view where an analysis result of the example 2C is output.

Note that FIG. 17A to FIG. 17C represent the analysis results when the deformation from FIG. 16A to FIG. 16B proceeded for 20%.

Accordingly, in the example 2A and the example 2B, when the fracture analysis of the spot welded portion was performed, the fracture analysis part 30 adjusted the sheet thickness such that it apparently became the two-layer spot welded portion. Specifically, the fracture analysis part 30 performed the fracture analysis of the connection part between the steel sheet A and the steel sheet B among the three pieces of the steel sheet A, the steel sheet B, and the steel sheet C by using a value of a sheet thickness of the steel sheet A and a value in which sheet thicknesses of the steel sheet B and the steel sheet C were added. Besides, the fracture analysis part 30 performed the fracture analysis of the connection part between the steel sheet C and the steel sheet B by using a value of a sheet thickness of the steel sheet C and a value in which sheet thicknesses of the steel sheet A and the steel sheet B were added.

Besides, in the example 2A, the fracture analysis part 30 applied the effective width B which was set as the shortest distance among the distance between spots L1, the distance between edges L2×2, and the distance between edge lines L3×2.

In the example 2A illustrated in FIG. 17A, the fractures occurred at six pieces among 10 pieces of the spot welded portions, and it was the same number as the number of actually fractured portions. Besides, in the example 2B illustrated in FIG. 17B, the fractures occurred at five pieces among the 10 pieces of the spot welded portions, and it was slightly different from the number of actually fractured portions. On the other hand, in the comparative example 2C illustrated in FIG. 17C, the fractures occurred at three pieces among the 10 pieces of the spot welded portions, and it was largely different from the number of actually fractured portions.

As stated above, the three-layer spot welded portion is determined by using the flowchart illustrated in FIG. 10, further the effective width B is set by using the flowchart illustrated in FIG. 12, and thereby, it is possible to improve the accuracy of the fracture analysis of the collision simulation in addition to largely reduce the preparation setting time. In particular, the effect becomes obvious as the number of spot welded portions increases to several hundred pieces, several thousand pieces.

Hereinabove, the present invention is described together with various embodiments, but the present invention is not limited thereto, and modification and so on within a scope of the present invention are possible.

INDUSTRIAL APPLICABILITY

The present invention can be used for, for example, a fracture analysis such as a collision simulation.

The invention claimed is:

1. An analyzing method of a spot welded portion, comprising:
   acquiring bar elements by which the spot welded portion to be analyzed is modeled;
   extracting other bar elements existing at a periphery of a target bar element which is targeted among the acquired bar elements;
   determining whether or not there is a bar element which shares the same end point with the target bar element among the extracted bar elements, by comparing an end point of the target bar element and an end point of the extracted bar elements;
   determining that the target bar element and the bar element which shares the same end point with the target bar element are a three-layer spot welded portion where three pieces of plate materials are stacked and spot welded when it is determined that there is the bar element which shares the same end point with the target bar element; and
   determining whether or not there is a bar element whose distance between the extracted bar elements and the target bar element is within a predetermined distance among the extracted bar elements when it is determined that there is not the bar element which shares the same end point with the target bar element, and determining that the target bar element and the extracted bar element are not the three-layer spot welded portion when it is determined that there is not the bar element within the predetermined distance,
   wherein the distance between the extracted bar elements and the target bar element is a distance between the end point of the extracted bar element and the end point of the target bar element on a common plate material, and the predetermined distance is a thickness of the plate materials or a nugget diameter of the spot welded portion.

2. The analyzing method of the spot welded portion according to claim 1, further comprising:
selecting a bar element whose distance between the end point of the extracted bar elements and the end point of the target bar element is the shortest among the extracted bar elements as an object bar element when it is determined that there is the bar element whose distance between the end point of the extracted bar elements and the end point of the target bar element is within the predetermined distance among the extracted bar elements;
determining whether or not the target bar element and the object bar element weld at least one same plate material;
determining whether or not the target bar element and the object bar element each weld the same plate materials when it is determined that the target bar element and the object bar element weld at least one same plate material; and
determining that the target bar element and the object bar element are the three-layer spot welded portion when it is determined that the target bar element and the object bar element do not each weld the same plate materials.

3. The analyzing method of the spot welded portion according to claim 2, further comprising:
determining that the target bar element and the object bar element are a two-layer spot welded portion where two pieces of plate materials are stacked and spot welded and they each spot-weld different plate materials when it is determined that the target bar element and the object bar element do not weld at least one same plate material.

4. The analyzing method of the spot welded portion according to claim 2, further comprising:
determining that the target bar element and the object bar element are the two-layer spot welded portion where two pieces of plate materials are stacked and spot welded and they each spot-weld the same plate materials when it is determined that the target bar element and the object bar element each weld the same plate materials.

5. The analyzing method of the spot welded portion according to claim 1, further comprising:
changing the target bar element to be the extracted bar element when it is determined that there is not the bar element whose distance between the end point of the extracted bar elements and the end point of the target bar element is within the predetermined distance among the extracted bar elements.

6. The analyzing method of the spot welded portion according to claim 1, further comprising:
calculating a distance from an end point of a target bar element which is targeted among the acquired bar elements to an end point of a shortest bar element existing on a common component with the target bar element as a distance between spots;
calculating a distance from the target bar element to a shortest edge as a distance between edges;
calculating a distance from the target bar element to a shortest edge line as a distance between edge lines; and
setting a minimum value among a value of the distance between spots, a value in which the distance between edges is doubled, and a value in which the distance between edge lines is doubled as an effective width B of the spot welded portion.

7. A non-transitory computer readable recording medium recording an analyzing program of a spot welded portion causing a computer to execute:
acquiring bar elements by which the spot welded portion to be analyzed is modeled;
extracting other bar elements existing at a periphery of a target bar element which is targeted among the acquired bar elements;
determining whether or not there is a bar element which shares the same end point with the target bar element among the extracted bar elements, by comparing an end point of the target bar element and an end point of the extracted bar elements;
determining that the target bar element and the bar element which shares the same end point with the target bar element are a three-layer spot welded portion where three pieces of plate materials are stacked and spot welded when it is determined that there is the bar element which shares the same end point with the target bar element; and
determining whether or not there is a bar element whose distance between the extracted bar elements and the target bar element is within a predetermined distance among the extracted bar elements when it is determined that there is not the bar element which shares the same end point with the target bar element, and determining that the target bar element and the extracted bar element are not the three-layer spot welded portion when it is determined that there is not the bar element within the predetermined distance,
wherein the distance between the extracted bar elements and the target bar element is a distance between the end point of the extracted bar element and the end point of the target bar element on a common plate material, and the predetermined distance is a thickness of the plate materials or a nugget diameter of the spot welded portion.

8. An analyzing apparatus of a spot welded portion, comprising:
processing circuitry configured to:
acquire bar elements by which the spot welded portion to be analyzed is modeled;
extract other bar elements existing at a periphery of a target bar element which is targeted among the acquired bar elements;
determine whether or not there is a bar element which shares the same end point with the target bar element among the extracted bar elements, by comparing an end point of the target bar element and an end point of the extracted bar elements; and
determine that the target bar element and the bar element which shares the same end point with the target bar element are a three-layer spot welded portion where three pieces of plate materials are stacked and spot welded when it is determined that there is the bar element which shares the same end point with the target bar element, and determine whether or not there is a bar element whose distance between the extracted bar elements and the target bar element is within a predetermined distance among the extracted bar elements when it is determined that there is not the bar element which shares the same end point with the target bar element, and which determines that the target bar element and the extracted bar element are not the three-layer spot welded portion when it is determined that there is not the bar element within the predetermined distance,
wherein the distance between the extracted bar elements and the target bar element is a distance between the end point of the extracted bar element and the end point of the target bar element on a common plate material, and the predetermined distance is a thickness of the plate materials or a nugget diameter of the spot welded portion.

* * * * *